(12) United States Patent
Tandiya

(10) Patent No.: US 10,130,400 B2
(45) Date of Patent: Nov. 20, 2018

(54) INTERLOCKING NAIL

(71) Applicant: Nitesh Kumar Tandiya, Madhya Pradesh (IN)

(72) Inventor: Nitesh Kumar Tandiya, Madhya Pradesh (IN)

(*) Notice: Subject to any disclaimer, the term of this patent is extended or adjusted under 35 U.S.C. 154(b) by 0 days.

(21) Appl. No.: 15/503,009

(22) PCT Filed: Oct. 10, 2014

(86) PCT No.: PCT/IB2014/065204
§ 371 (c)(1),
(2) Date: Feb. 10, 2017

(87) PCT Pub. No.: WO2016/024149
PCT Pub. Date: Feb. 18, 2016

(65) Prior Publication Data
US 2017/0224394 A1    Aug. 10, 2017

(30) Foreign Application Priority Data

Aug. 12, 2014    (IN) .......................... 2601/MUM/2014

(51) Int. Cl.
*A61B 17/72* (2006.01)
*B25C 1/00* (2006.01)

(52) U.S. Cl.
CPC .......... *A61B 17/7241* (2013.01); *A61B 17/72* (2013.01); *A61B 17/7225* (2013.01); *A61B 17/7283* (2013.01); *B25C 1/00* (2013.01)

(58) Field of Classification Search
CPC . A61B 17/7241; A61B 17/72; A61B 17/7225; A61B 17/7283; B25C 1/00
USPC ................................................ 606/62, 64, 67
See application file for complete search history.

(56) References Cited

U.S. PATENT DOCUMENTS

| 5,697,930 A | 12/1997 | Itoman et al. |
| 5,766,174 A | 6/1998 | Perry |
| 6,106,528 A * | 8/2000 | Durham ............. A61B 17/1707 606/62 |
| 8,157,802 B2 | 4/2012 | Elghazaly et al. |
| 8,491,584 B1 | 7/2013 | Fagan |
| 8,540,714 B2 | 9/2013 | Gordon et al. |
| 2006/0189988 A1 | 8/2006 | Schlienger et al. |
| 2007/0276385 A1 | 11/2007 | Schlienger et al. |

* cited by examiner

*Primary Examiner* — Pedro Philogene
*Assistant Examiner* — David C Comstock
(74) *Attorney, Agent, or Firm* — PatShegen IP; Eva Taksel

(57) ABSTRACT

The invention relates to an interlocking nail (10) for fixation of transverse and short spiral fractures of, long bone, particularly shaft of the femur, tibia and humerus, having Graft extrusion space/slot (101) for holding stem cells graft and 4 or 5 holes for putting interlocking bolts from lateral to medial direction. Constant compression achieved (irrespective of weight bearing cycle) at the fracture site by tightening of the Endo-Compression Screws (108, 109 and 110) results in stimulation of stem cells and reduction in bone gap, thus enhances bone healing and union manifolds.

17 Claims, 18 Drawing Sheets

INTERLOCKING NAIL

This application claims priority benefit of Indian Patent Application No. 2601/MUM/2014 filed on Aug. 12, 2014.

FIELD OF INVENTION

This invention relates to an interlocking nail for fixation of transverse and short spiral fractures of, long bone, particularly shaft of the femur, tibia and humerus with the mechanism provided in the invention to augment the bone healing and union manifolds. The disclosed interlocking nail specification could also be used for fractures of the radius and ulna.

BACKGROUND OF ART

The intramedullary fixation devices had been in existence since 1940. The Interlocking Nail is a cylindrical hollow rod connected with the sets of 2 or 3 screws on either ends. Since then, few minor modifications such as increase in the number of screws were introduced in the design/structure of the interlocking nail.

The interlocking screw provides the rotational stability at the fracture site and improves the Nail-Bone Construct stability. However no improvement in fracture biology is seen. Further, the prior art does not discuss about extra compression at the fracture provided by interlocking nail.

Indian Patent Application 1088/MUMNP/2005 provides an intramedullary nail for the fixation of fractures of the proximal femur, with a femur neck screw, installable with a proximal femur nail, into the intramedullary area, by a diagonal bore, running to the longitudinal axis of the femur nail, from the side of the femur nail, and a locking element with at least one branch parallel to the axis of the femur neck screw. The connection between the locking element and a groove in the bore of the femur nail forms a twisting lock of the femur neck screw and allows for the axial movement of the femur neck screw in the bore of the femur nail.

Indian Patent Application No. 3544/DELNP/2005 provides an intramedullary nail that has a distal end suitable for insertion in the medullary space. The intramedullary nail has several cross holes with a hole axis, each of which defines a virtual drill cylinder with a cylinder axis corresponding to the hole axis of the defining cross hole. The drill cylinders of at least two cross holes penetrate each other. The cylinder axis of the two mutually penetrating drill cylinders do not have any common intersection point on the longitudinal axis, resulting in improved mechanical strength without any need for the size of the cross section of the medullary nail to be increased.

Indian Patent Application No. 3986/DELNP/2012 provides systems, devices and methods for limiting compression of a fracture imposed by a lag screw of a fixation system that includes a fixation device, a lag screw and a compression screw. The disclosed devices, systems and methods prevent over-compression of a fracture by a lag screw caused by over rotation of the compression screw.

Indian Patent Application 3656/DELNP/2006 provides an intramedullary nail designed in particular for the tibia and has three distinct locking sections with at least one through-hole each for receiving locking screws. The said three locking sections are separated from each other by two distinct intermediate sections having less through-holes (8) per length unit than each of the locking sections (5, 6, 7).

The intra-medullary nails mentioned above for fixation of fractures are inserted in the medullary space. However, none of the prior art discusses about the improved and enhanced healing of the bone irrespective of the weight bearing cycle. The present invention relates to increasing bone healing due to the continuous compression caused by the Endo-Compression Screw that is inbuilt in the interlocking system. Additionally, none of the prior arts suggest the use of auto graft (i.e cancellous bone graft) in the interlocking nail obtained from medullary cavity of bone which is being operated.

SUMMARY OF THE INVENTION

The invention relates to an interlocking nail for fixation of transverse and short spiral fractures of, long bone particularly shaft of femur, tibia and humerus, having slot for holding plurio-potent mesenchymal stem cells derived from auto-graft particularly canacellous bone graft. The interlocking nail has 4 or 5 holes for putting interlocking bolts from lateral to medial direction or from medial to lateral direction or in anterio-posterior direction, depending on orientation of interlocking hole. Constant compression at the fracture site is achieved (irrespective of weight bearing cycle) by tightening of the Endo Compression Screw at the proximal end of the interlocking nail resulting in the stimulation of mesenchymal stem cells due to compression as well as reduction in gap at fracture site, thus enhances bone healing and union manifolds.

Accordingly the principal object of the invention is to introduce an interlocking nail for fixation of transverse and short spiral fractures of, the long bone.

Another object of the invention is to provide a slot in the interlocking nail for holding mesenchymal stem cells graft, preferably from cancellous bone graft which helps in the enhanced healing and fixation of fracture. The said graft is obtained from medullary cavity of bone which is being operated. This particular slot should match with fracture site.

It is another object of the invention to introduce a longitudinal threading inside the Interlocking Nail and tightening of the Endo-Compression Screw in the thread.

It is another object of the invention to provide a Graft Stop-Endo Screw inside the nail for holding the cancellous bone graft at the fracture site and Graft Compression Endo screw for compressing the bone graft thus allowing bone graft cell compression as well as cell migration across the fracture site.

It is another object of the invention to provide long graft extrusion space which threads internally to allow egress of graft cells maximum at fracture site via movement of Graft Endo-Compression screw and same could be modified as per the requirement.

It is another object of the invention to maintain the strength of the nail bone construct by providing hole in the graft extrusion space from medial to lateral direction (i.e. side to side) not from front to back (anterior to posterior).

It is another object of the invention to thread Graft Extrusion Space, 10 mm above margin of the graft and 5 mm below this space. The space of 10 mm allows the movement of the stem cells from auto-graft for bone healing from inside the nail.

A further object of the invention is to achieve a static compression with tightening of the Endo Compression Screw, at fracture site irrespective of weight bearing cycle resulting in enhanced bone healing due to stimulation of stem cells, particularly plurio-potent mesenchymal stem cells that divide into the osteoblast to form new bone.

BRIEF DESCRIPTION OF THE DRAWINGS

The present invention may be better understood and its numerous objects, features and advantages made apparent to those skilled in the art, by referring to the accompanying drawings.

Note:
(1) The whole mechanism of action in the presenting interlocking nail is demonstrated with fixation of transverse fracture of shaft the femur only in stepwise manner.
(2) The same internal mechanism is used for interlocking nail for the tibia, the humerus and radius and ulna bone.

DESCRIPTION OF THE INVENTION

The detailed description of the appended drawings is intended as a description of the currently preferred embodiments of the present invention, and it is not intended to represent the only form in which the present invention may be practiced. This is to be understood that the same or equivalent functions may be accomplished by different embodiments that are intended to be encompassed within the spirit and scope of the present invention.

The present invention relates to an interlocking nail (10) for fixation of transverse and short spiral fractures of long bone particularly shaft of the femur, tibia and humerus. The disclosed interlocking nail specification could also be used for fractures of the radius and ulna.

The purpose of the present invention is as follows:
  To provide a mechanism resulting in the increase of compression forces at fracture site;
  To re-use the bone cells lost during reaming;
  To improve the bone biology locally at fracture site;
  To improve the healing time and reduce the nail failure rate.

Figure 1A:
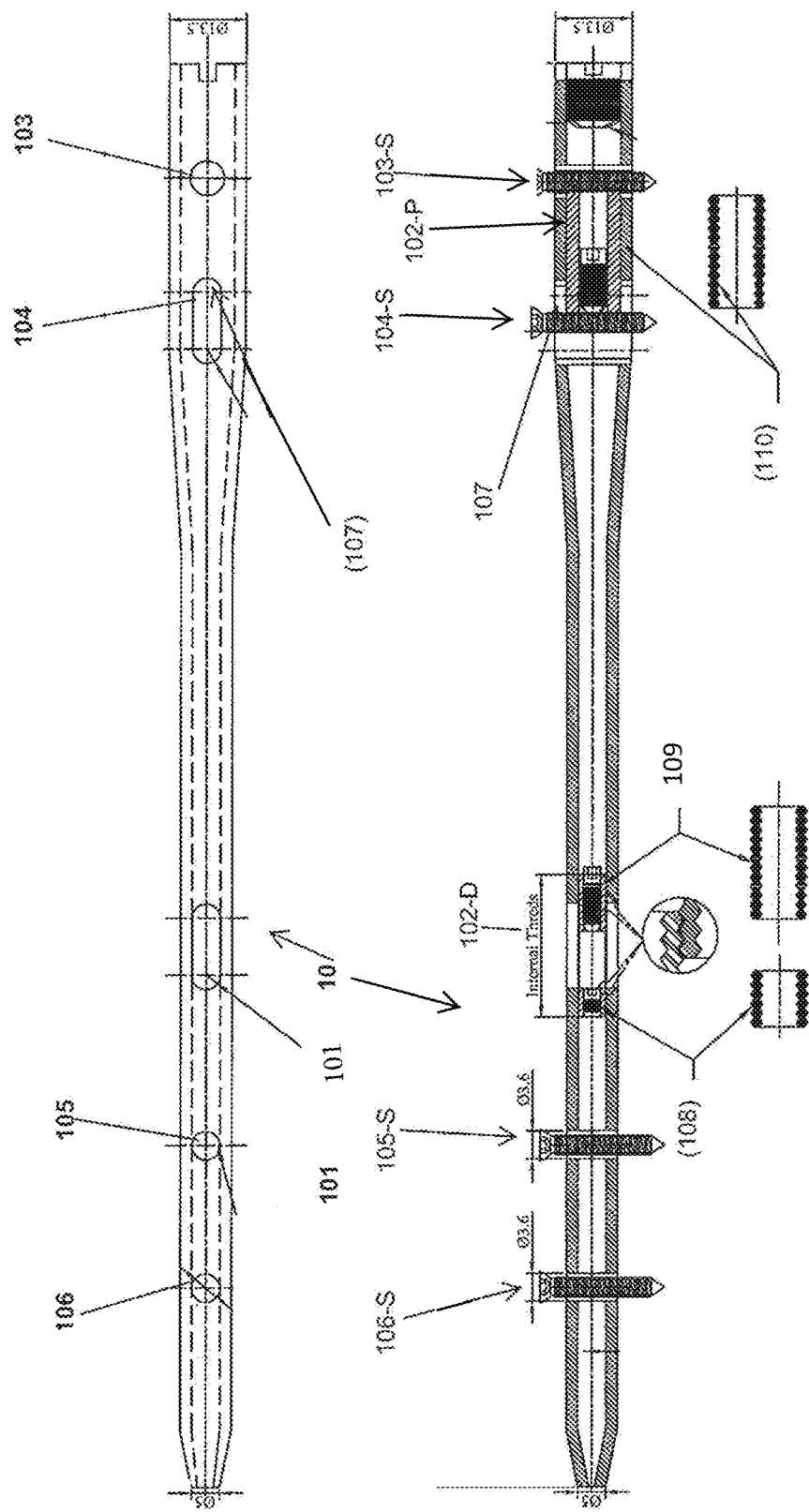
FIG. 1 (a) and (b) illustrates the schematic diagram of the Interlocking Nail;
  (a) Anterio-posterior and Lateral view of femur interlocking nail.
  (b) Anterio-posterior and Lateral view of tibial interlocking nail.
Figure 1:
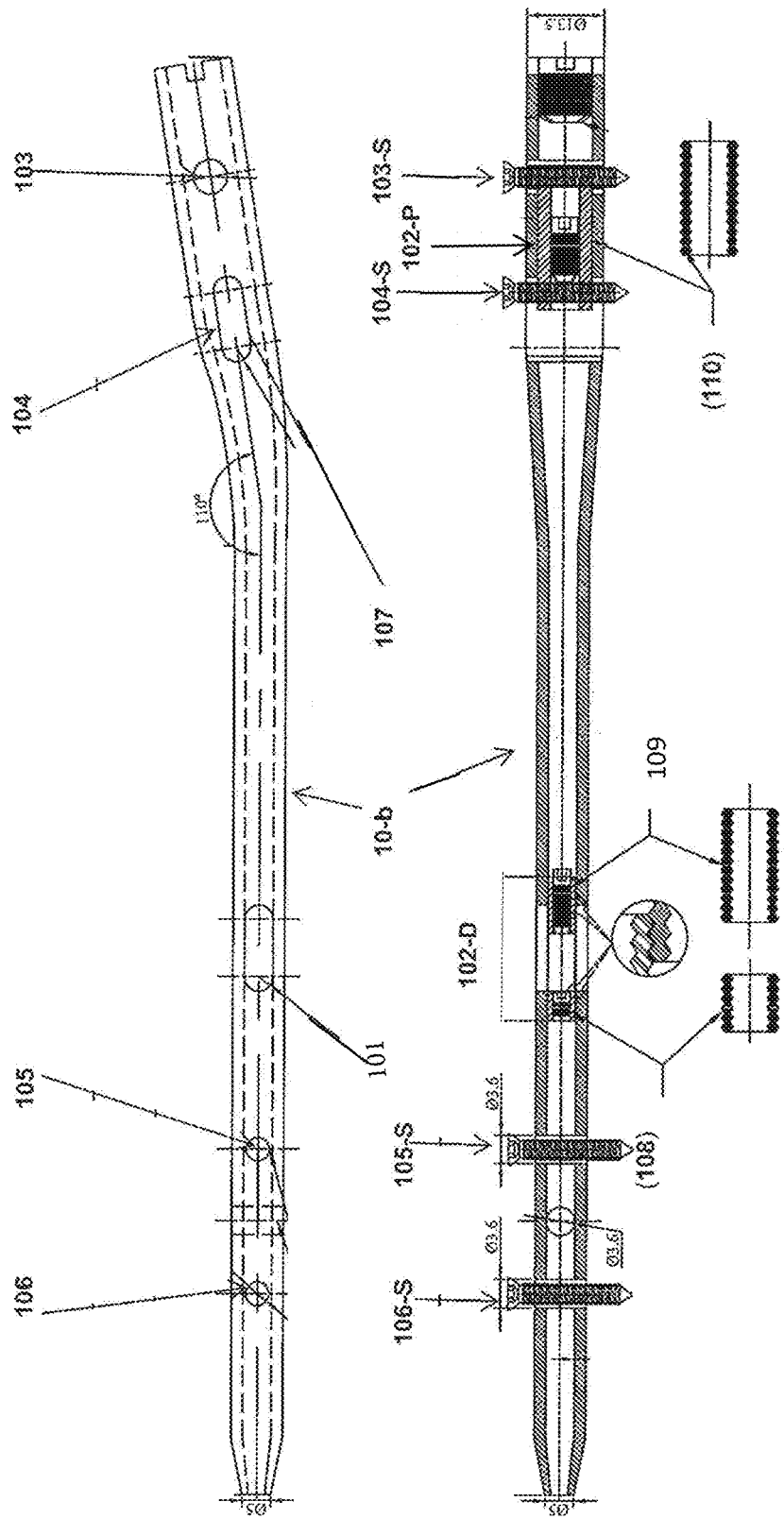
Figure 2:
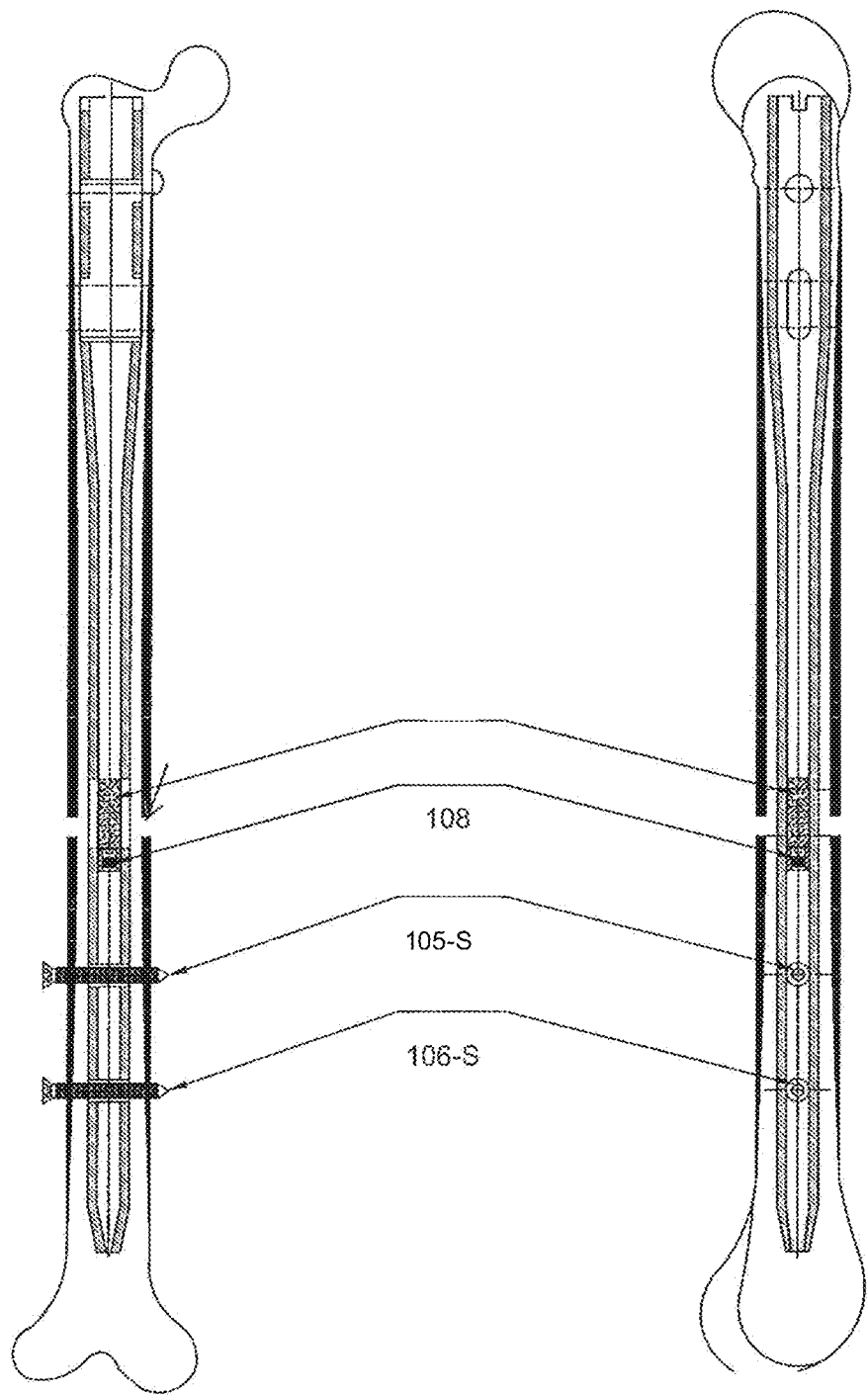
FIG. 2 showing the cancellous autograft inside the nail with Graft Stop-Endo Screw holding graft at the fracture site.
Figure 3:
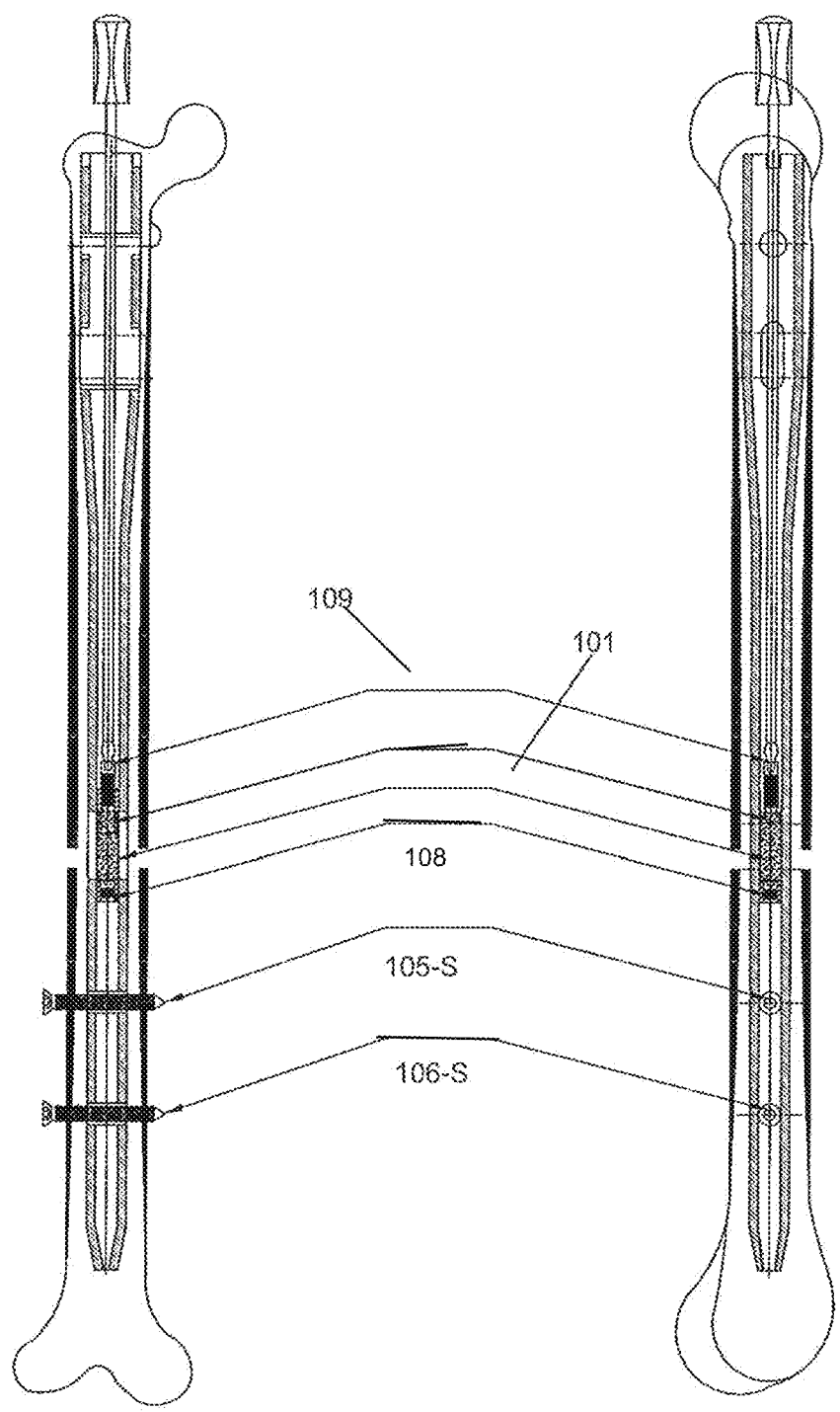
FIG. 3 showing introduction of Graft Compression Endo Screw.
Figure 4:
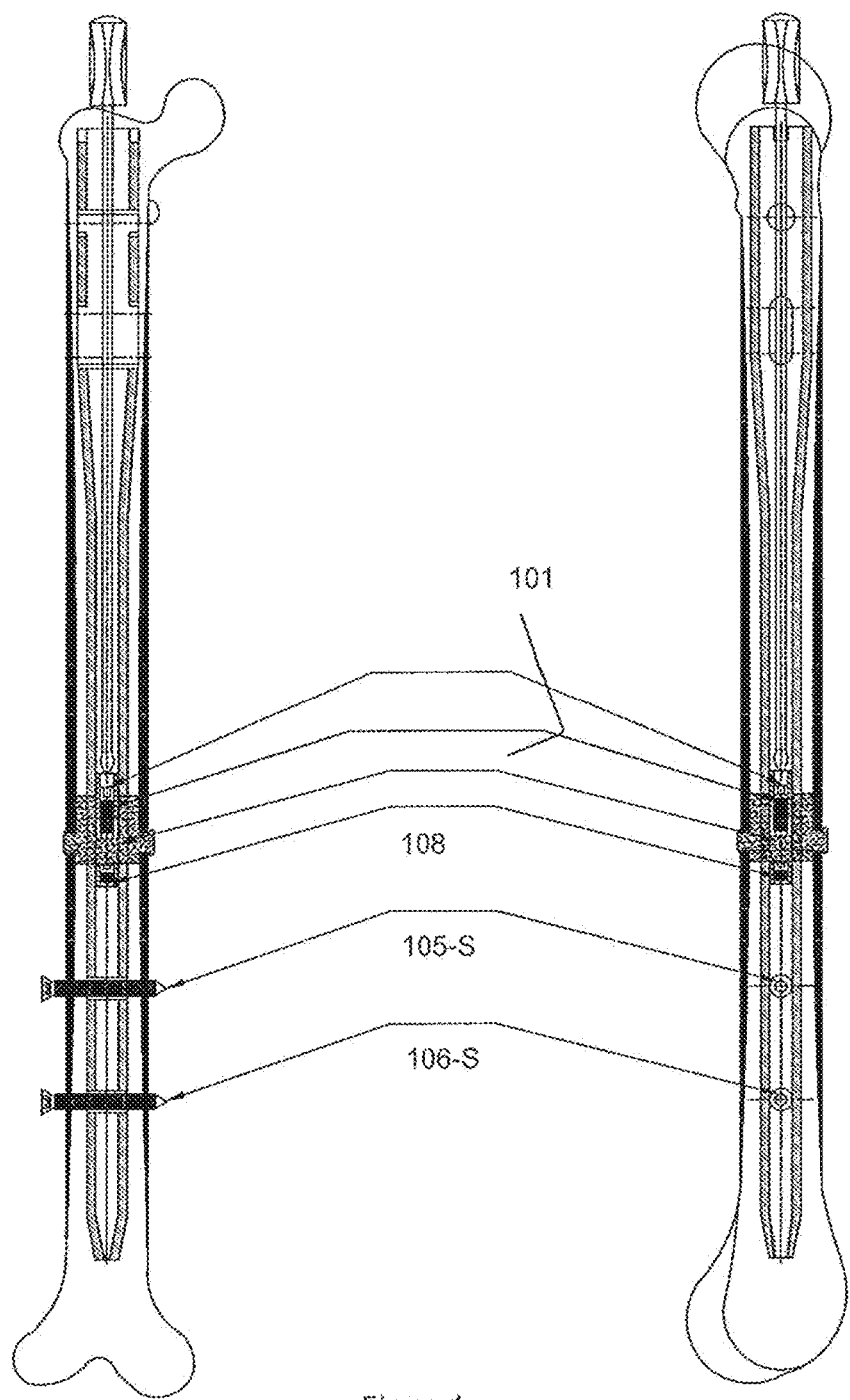
FIG. 4 showing migration of bone graft across fracture site due to the tightening of Graft Compression Endo Screw.
Figure 5:
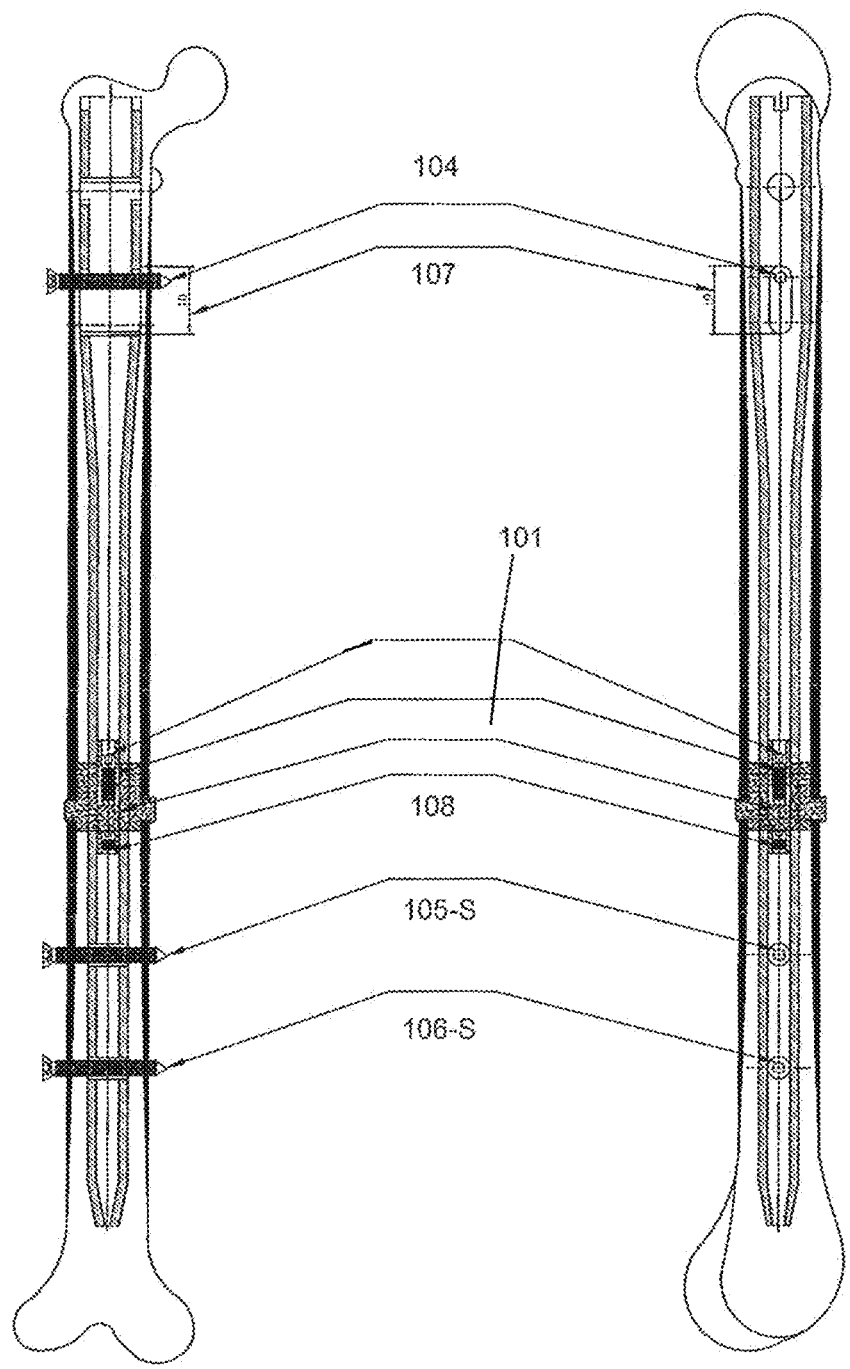
FIG. 5 showing introduction of $2^{nd}$ proximal screw in proximal end of dyanamisation hole.
Figure 6:
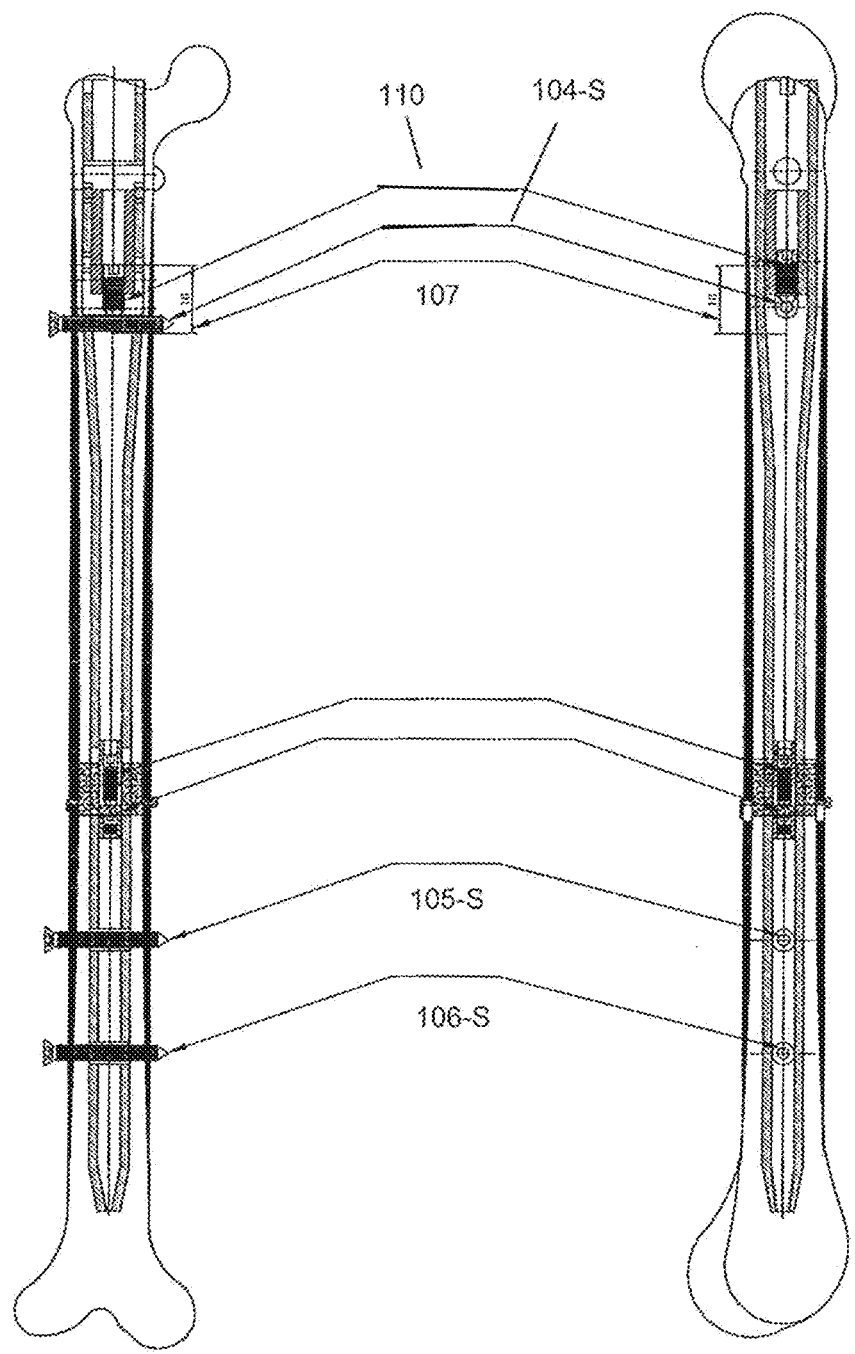
FIG. 6 showing introduction of Endo Compression Screw and reduction of gap at the fracture site by tightening of screw.
Figure 7:
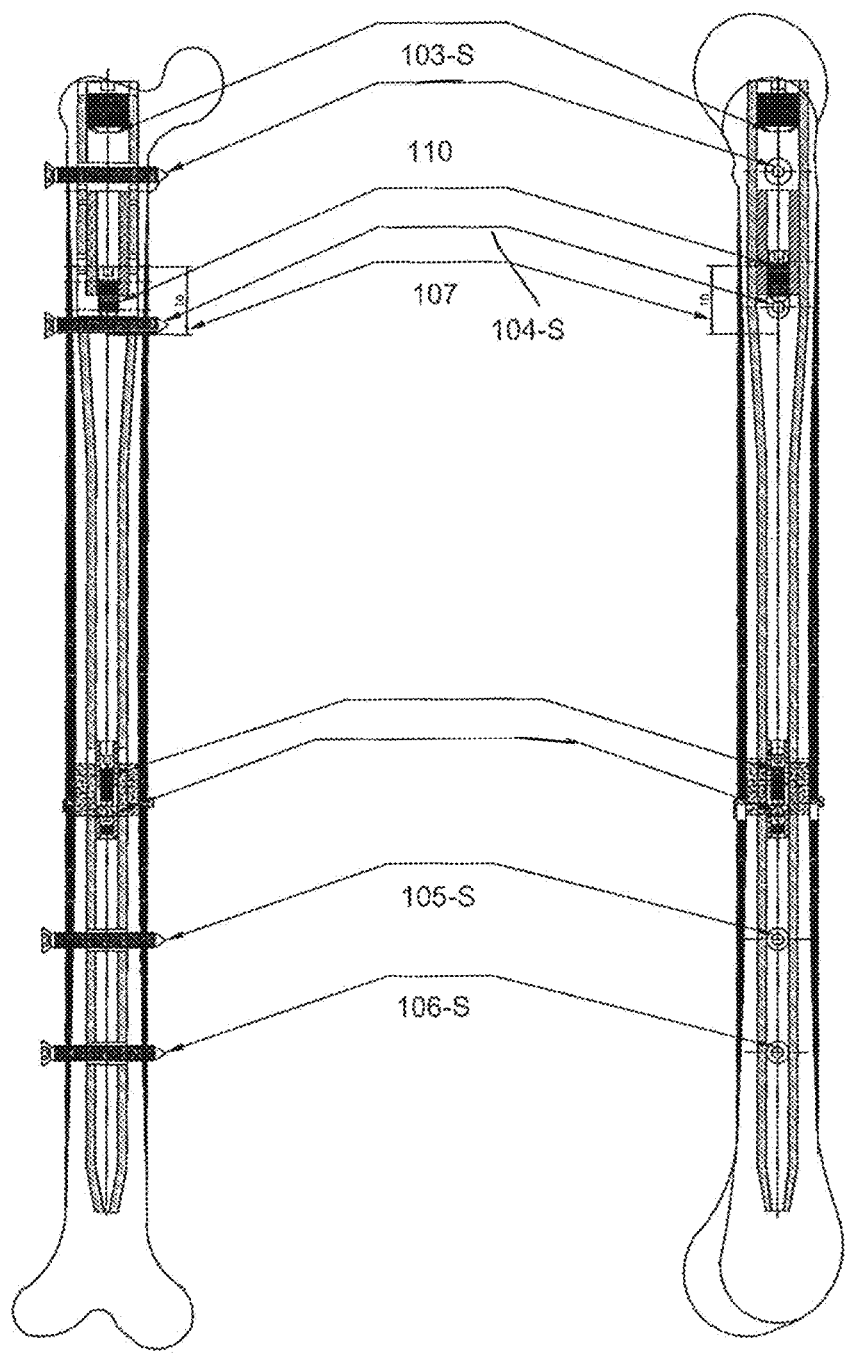
FIG. 7 showing introduction of remaining screw and final reduction of gap at the fracture site.
Figure 8:
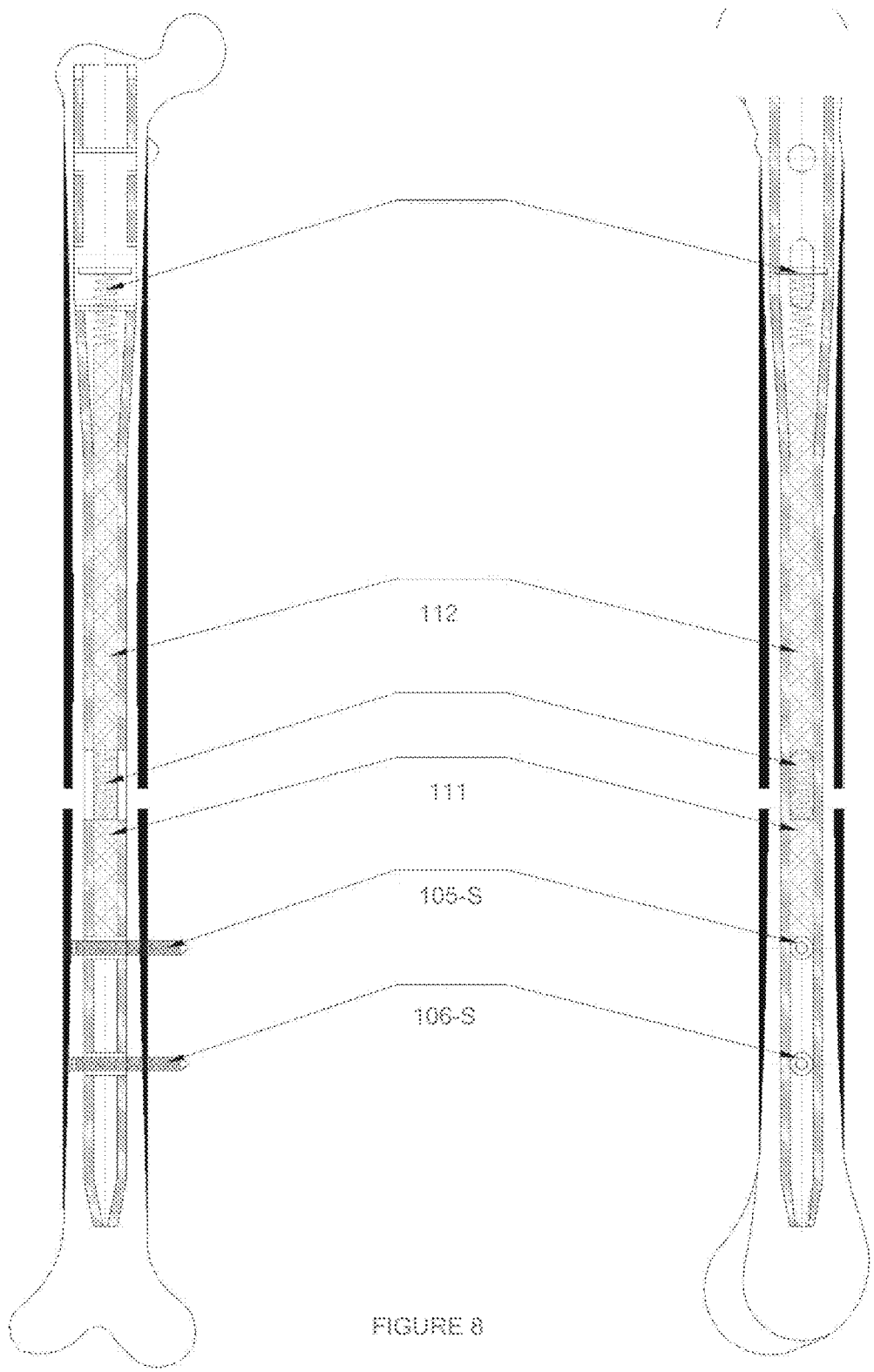
FIG. 8. showing the Distal Graft Blocking Plastic Plug (DGBPP) and Proximal Graft Compressive Plastic Plug (PGCPP) in place with the bone graft inside the nail.
Figure 9:
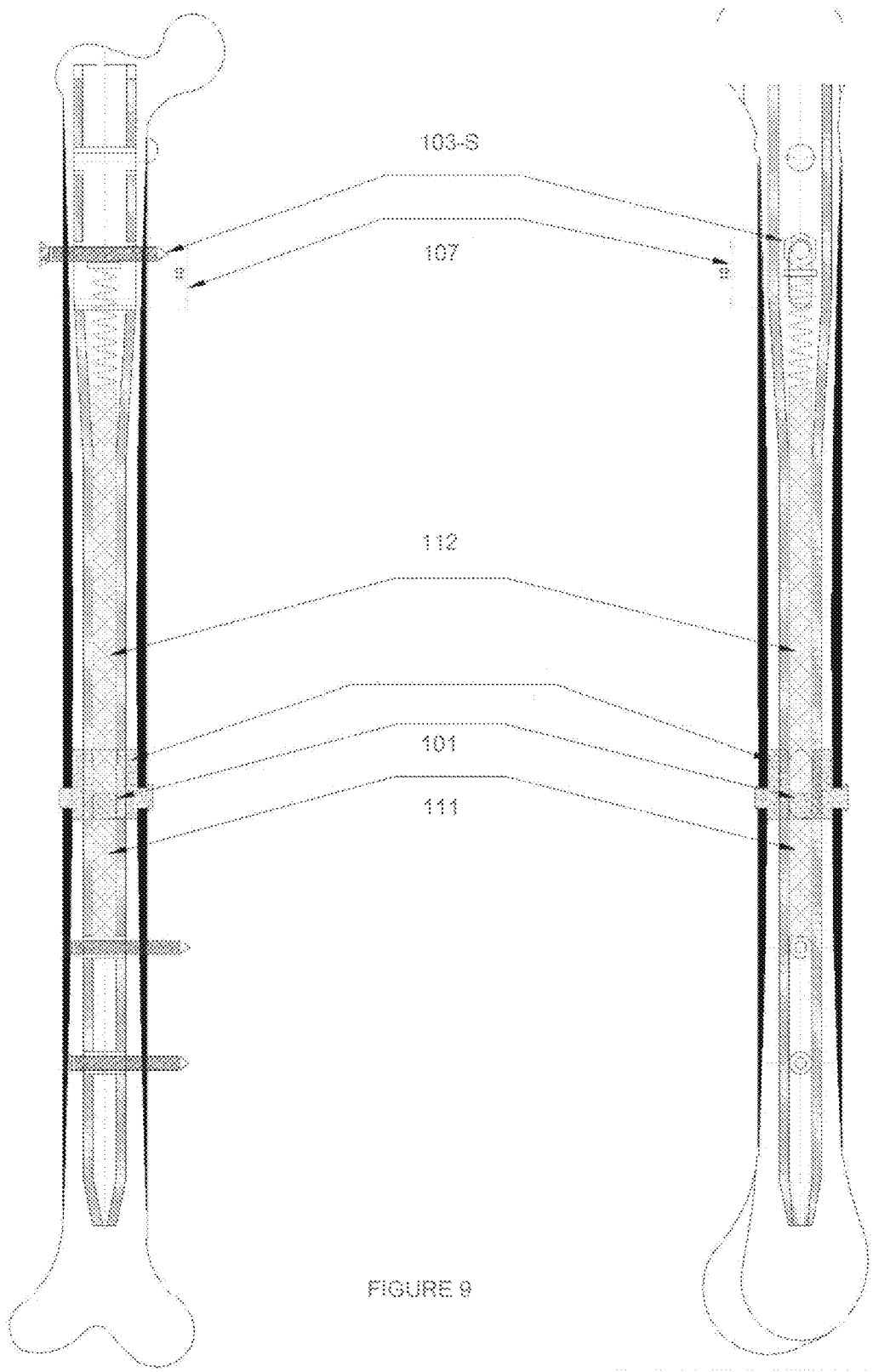
FIG. 9. showing outward movement of graft substances along the endo-osteal surface of bone and also through the fracture gap around the fracture.
Figure 10:
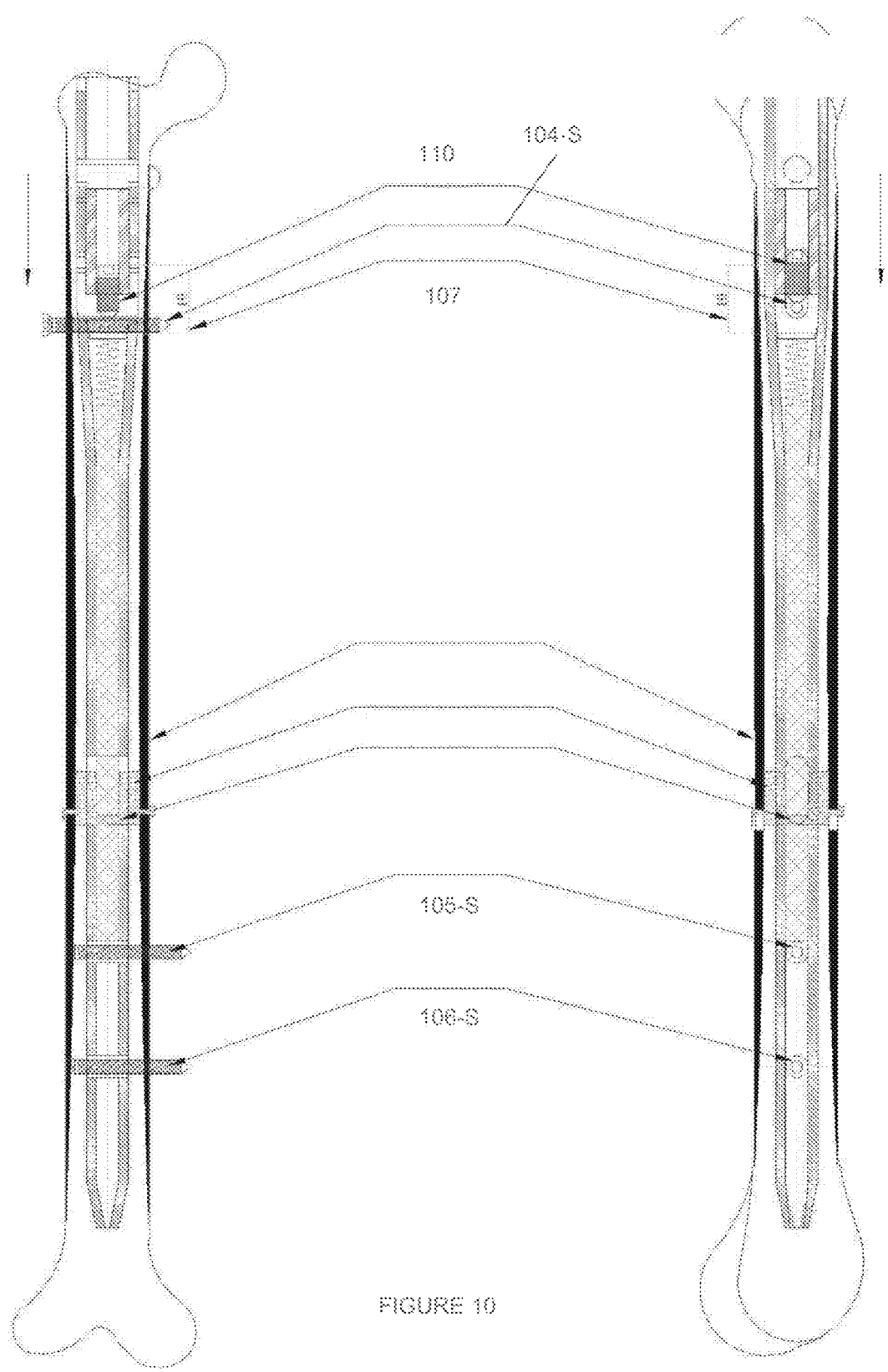
FIG. 10. showing introduction of Endo Compression Screw and reduction of gap at the fracture site by tightening of screw.
Figure 11:
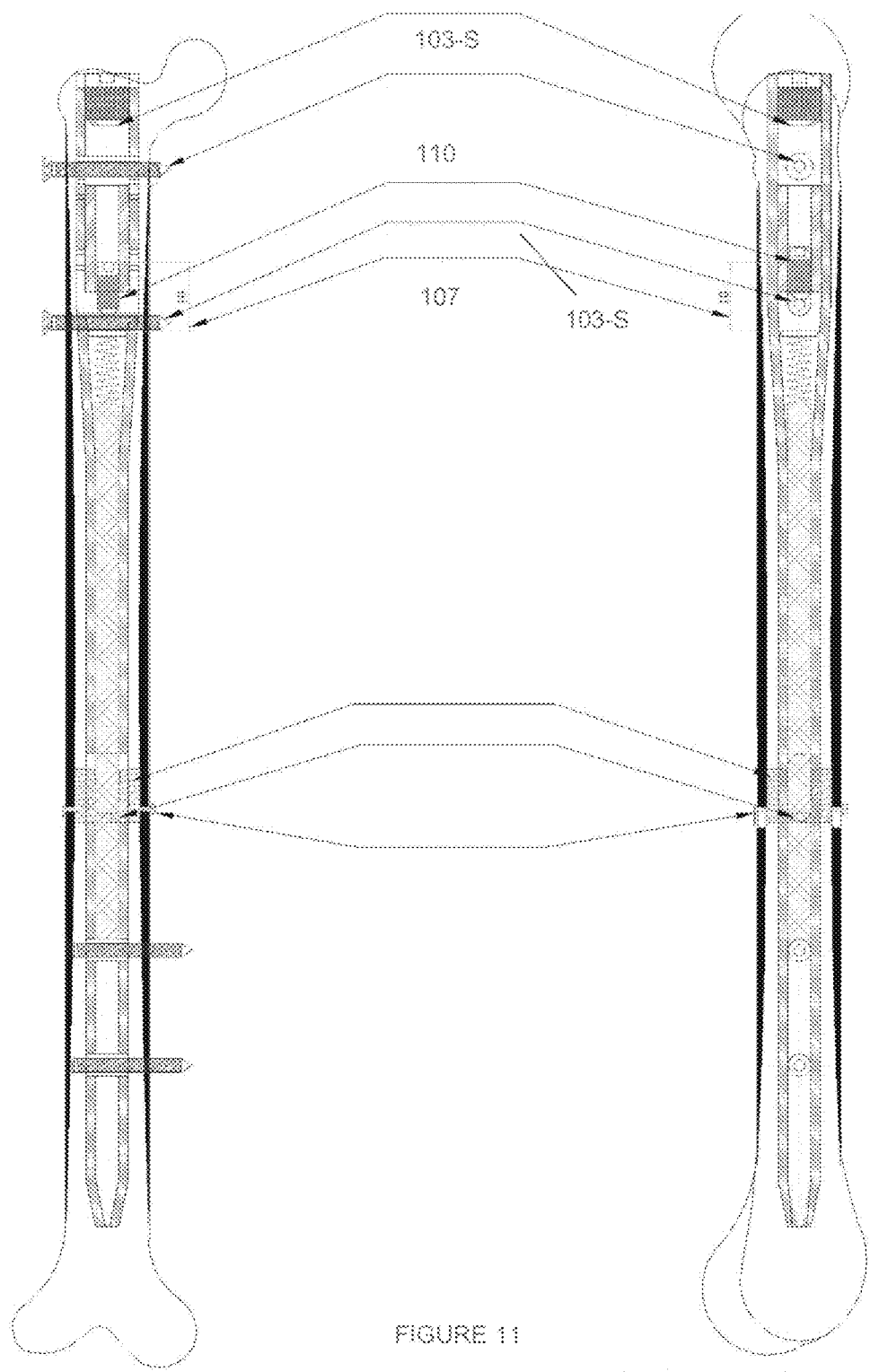
FIG. 11. showing the whole Nail-Bone Assembly.

In accordance with an embodiment of the present invention, the interlocking nail (10) is a hollow cylinder having an outer diameter ranging from 8 to 13 mm and length ranging from 260-400 mm. The length of the interlocking nail (10) is not limited to the aforesaid range, but may vary depending upon the length of the bone. The thickness of interlocking nail (10) is as per international protocol for nail. However for better understanding the thickness of the interlocking nail (10) as used, is 2 mm The shape of the interlocking nail (10) depends upon the bone type. For instance, [ref. FIG. 1(b)] in fixing the fracture of tibia, interlocking nail (10-b) is curved in its proximal part at an angle of 110° to accommodate the proximal angle of the bone. Similarly, in case of femur fractures, interlocking nail is slightly curved/bent anteriorly.

The graft extrusion space or slot (101) of 10 mm in length and 2 mm in height is created along the neutral axis of the nail (10). The slot (101) holds stem cells graft (plurio-potent mesenchymal stem), preferably from cancellous bone graft (autograft). The introduction of graft stem cells significantly accelerates healing and reduces fracture fixation or union time. A preoperative analysis is done in order to assess the exact location of the fracture and to determine the configuration of fracture. The position of the slot (101) for egress/extrusion of stem cells could be modified as per the preoperative analysis of fracture and interlocking nail (10) is chosen with a slot (101) which matches with the fracture site.

The added advantage herein is the use of bone cells from the bone being operated and providing constant static compression across the fracture site.

The length of the graft extrusion space (101) is about 10 mm, which is from medial to lateral direction i.e. from side to side. The whole part of the graft extrusion space (101) is threaded internally. The internal thread (102-D) begins from 10 mm above margin of graft extrusion space (101) and 5 mm below the said space (101). The slight space between the nail surface and bone surface allows the movement of the stem cells for the bone healing from inside the nail, to the fracture site and along the endo-osteal surface.

In the standard interlocking nail (10) for long bone fracture, 4 or 5 holes are present for fixing interlocking bolts from lateral to medial direction or from medial to lateral direction or in anterio-posterior direction, depending on orientation of interlocking hole. These holes are oriented along the line perpendicular to central axis of nail and on opposing surface, across whole thickness at the corresponding level. Two holes are present at proximal part (103 and 104) and two holes (105 and 106) are present at distal part of nail (10). However, the number of holes and angle of screw insertion could be modified as per requirement.

Unlike the second proximal hole (104), first proximal hole (103) is same as found in other available interlocking nails. The second proximal hole (104) in the interlocking nail (10) would be of 10 mm in length and quadra-angular in shape with curved margin. Screw is inserted in the most proximal part, i.e. in upper end of dynamisation hole (107). As already discussed internal thread (102-P) starts about 5 mm above the second proximal hole (104) and covering $\frac{3}{4}^{th}$ of internal surface of hole.

This internal threading (102-D) leads to compression of bone graft between Graft Stop Endo Screw (108) and Graft Compression Endo Screw (109) which creates constant static compression resulting in:

better approximation of bony end and leads to transfer of axial forces;

reduces bone gap, therefore bone cells have to travel less for bridging the gap;

reduced bone gap means less distance between the harversian canal system and thus early restoration of bone vascularity and bone healing by stimulating pluriopotent stem cell for bone formation and bone healing.

The Graft Stop-Endo Screw (108) is introduced inside nail (10), after putting all interlocking bolts (105-S and 106-S) in distal holes (105 and 106) of the nail (10). The Graft Stop-Endo Screw (108) inside the nail (10) holds the cancellous bone graft, approximately 3 mm, below the level of the fracture line. The Graft Compression Endo Screw (109) is then inserted inside the nail, at desired level. With the tightening of the Graft Compression Endo Screw (109), the graft is compressed between two endo screws (108 and 109), results in the migration of cells from the space provided in nail at the fracture site. These cells also cross the fracture site and come to lie under peri-osteum. Some cells migrate along the endo-osteal surface both in proximal and distal direction across the fracture site. Compression of graft would also stimulate plurio-potent stem cells to divide into osteoblast that will further enhance fracture healing.

It is significant to note that nail failure occurs because there is no strong bony bridge in early 7 weeks of healing that cause nail to share extra load for prolonged period of time. In order to overcome the said limitation a longitudinal screw is introduced inside the Endo Compression Screw of nail which exerts downward force on 2nd proximal screw and pulls distal fragment of fractured femur provided distal screws are anchored to bone and increase the contact area between fractured ends. Therefore, bone cells have to make less effort in order to bridge the gap because travel distance is reduced resulting in faster re-vascularization of bone, which further stimulates osteo-progenitor bone cells. Endo Compression Screw system is very effective in providing constant static compression at the fracture site and to help in "Effective De-loading" of the nail by virtue of firm bone opposition.

Even after fastening of the screw in the typical standard interlocking nail, a slight gap is left at the fracture site ranging from 1-5 mm, which in turn delays bone formation and healing. In order to overcome such limitation of standard interlocking nails, the present invention has devised Endo-Compression Screws (110) inside nail (10). After the lower proximal screw (104-S) is tightened, the compression screw (110) is inserted from the proximal end of the nail (10). The fracture is continuously compressed with tightening of the Endo Compression Screw (110), resulting in the movement at fracture site which is along the axis of nail (10). In turn maximum compression is achieved at the fracture site, irrespective of weight bearing cycle, results in enhanced bone healing. In addition to this, constant compression at fracture site enhances bone healing, due to stimulation of stem cells, particularly plurio-potent mesenchymal stem cell to divide into osteoblast that will further enhance healing.

Further both the Graft Endo Screws used are solid screws that cover most of the length of Graft Extrusion Space; therefore the concerned space in the question would be reduced in size. Thus strength of the nail would not be compromised significantly in any way.

Figure 12:
FIG. 12 showing Prototype 1.
Figure 13:
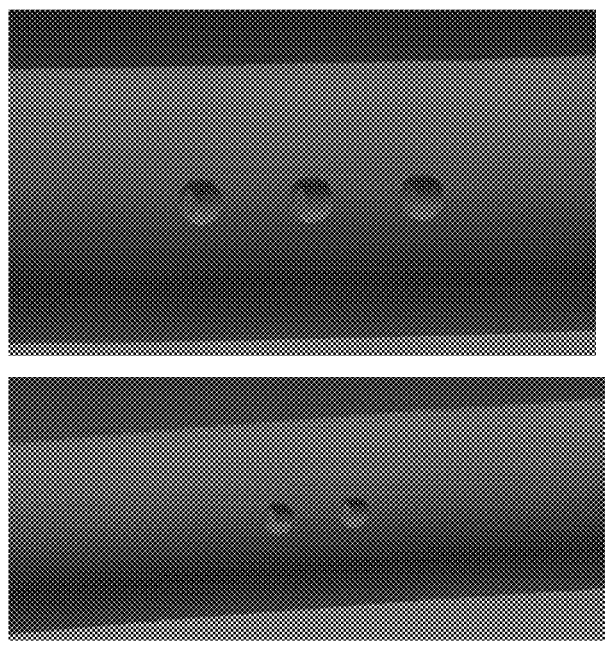
FIG. 13 showing staggered hole configuration.
Figure 14:
FIG. 14 showing Prototype 2.
Figure 15:
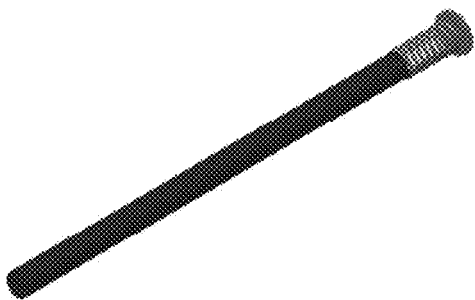
FIG. 15 showing Plastic Plug System.

Time frame for bony union can be improved with the help of the presenting prototypes. In both the Prototypes (1 and 2) holes or slots are provided for the bone cell delivery at the fracture site. Prototype-1 has 5-holes configuration which are on the medial-lateral face of the nail having a staggered configuration which passes through one wall of the nail only. (Refer FIG. 12).

In Prototype-1 after putting the Distal Graft Blocking Plastic Plug "DGBPP" (111) which is blocked by distal screw the bone graft and the marrow cells are inserted. Once the graft is inside with the help of metallic plunger, they are pushed further downwards to move them out of the nail due to pressure effect. Thereafter Proximal Graft Compressive Plastic Plug PGCPP (112) is inserted. On the upper end of PGCPP (112) metallic spring is attached. One end of metallic spring is buried in PGCPP (112) and another end is attached to metallic circular bar.

After putting 2nd proximal screw (104-S), the circular metallic disc is in close approximation to the said screw. On the top of transversely lying screw, Endo-Compression Screw (110) is introduced. When Endo-Compression Screw (110) is tightened along the longitudinal axis of nail, a compression force is generated in 2nd proximal screw (104-S), which is then transferred to PGCPP (112) via spring and metallic plate system provided. The compression force leads to activation and division of osteo-progenitor bone cells into bone forming cells.

In the Protoype-2 the slot configuration is used either on single face or both the opposing faces in the Medio-lateral plane. The dimension of slot is 2 mm in height and 10 mm in length along the neutral axis of the nail. The said dimension and orientation of slot has a minimum effect on the strength of the nail.

EXPERIMENTS

In order to predict the behaviour and practicality of prototype of interlocking nail (10) of the present invention, following experiments were performed.

a) Three Point Nail Bend Test and Nail Yielding Test

Figure 16A:
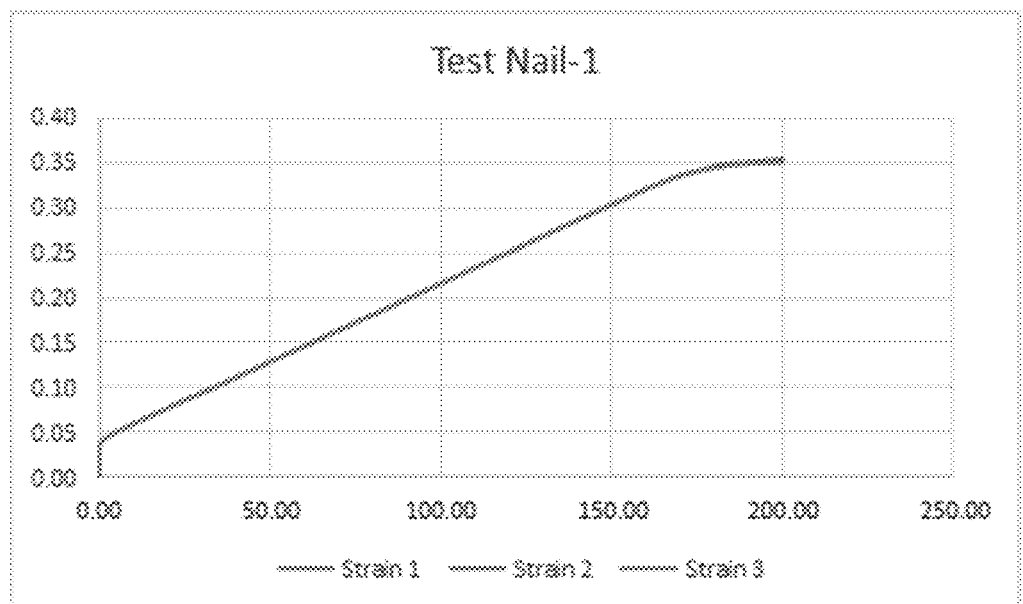
FIGS. 16A-16C are graph representations of point nail tests.
Figure 16B:
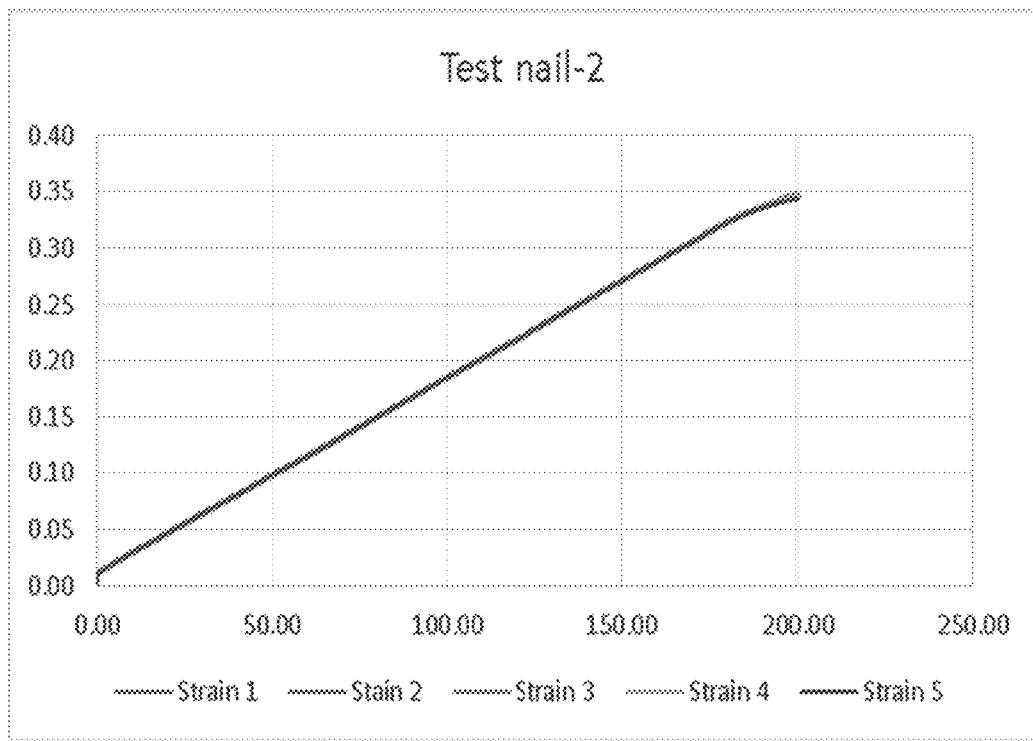
Figure 16C:
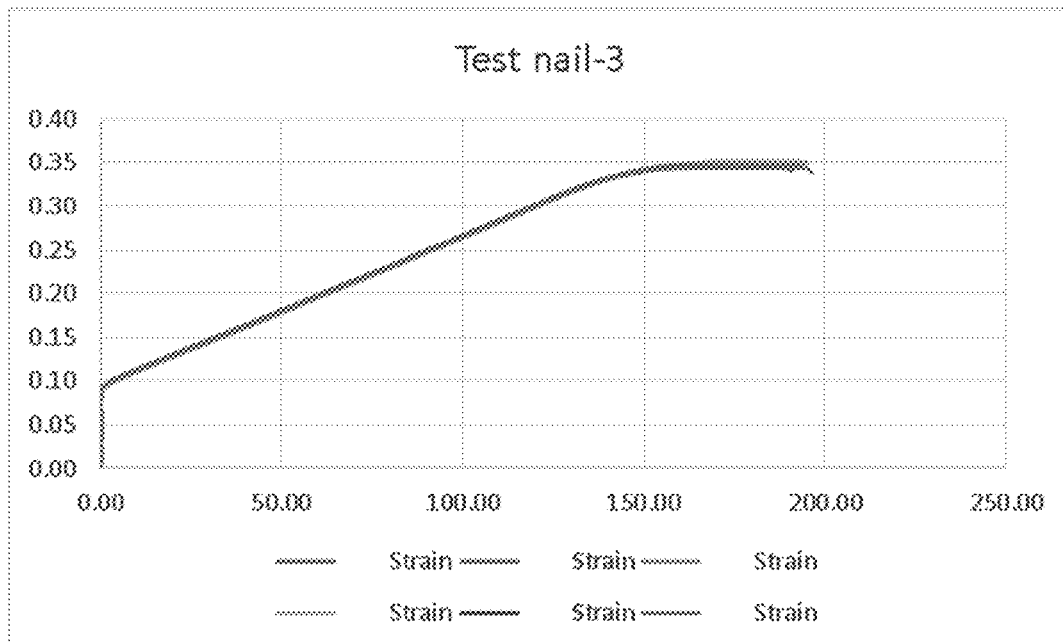
Figure 17:
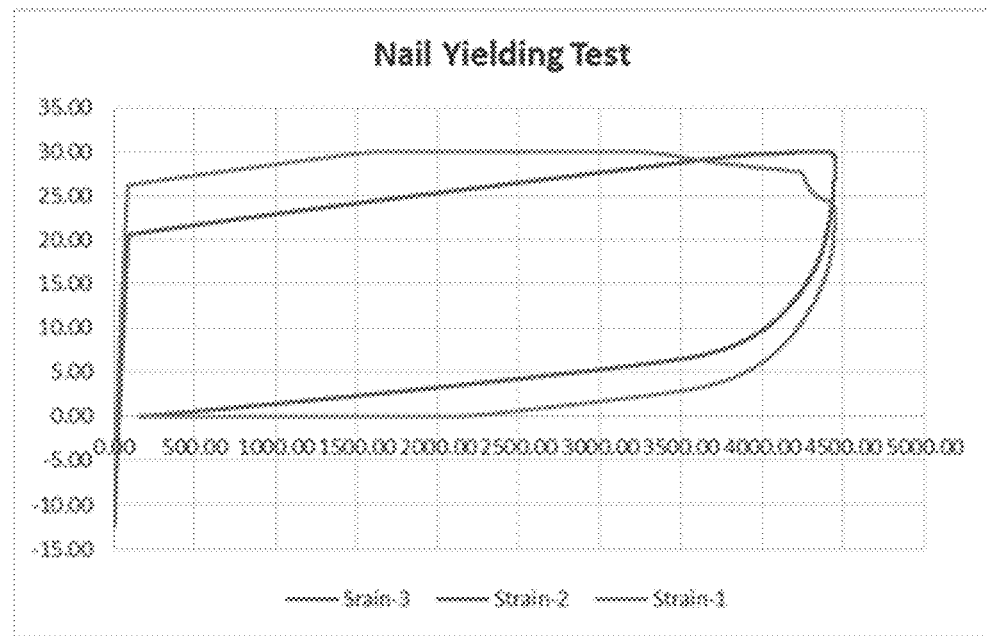
FIG. 17 is a graph representation of a nail yielding test.

Three point nail bend test was performed to assess the strength of the nail and the effect of making holes in different configuration at the central part of nail. The results of the three point nail bend test for three samples of nail are shown in the graph representations illustrated in FIGS. 16A-16C As shown in the graph representation of a nail yielding test illustrated in FIG. 17, there were no differences in the peak force require to yield the nail when force is applied to assess ultimate yielding force of test nails (1, 2, 3).

b) Feasibility of Graft Migration across the Slot or Holes

The results were optimum and encouraging. The bone graft oozed out of the hole/slot.

c) Effect of Compressive Mechanism on Translation of Bone

During the experimental trials mechanism of compressive screw worked flawlessly. The insertion of Endo-Compression screw in the nail can be attributed to the presence of $2^{nd}$ proximal hole for the said compressive mechanism.

d) Assessing different Configuration of Screw Holes or Slot and its Effect on Strength of Nail Using Finite Element Analysis On applying force along anterio-posterior plane, no indication of significant stress generation around the holes was observed. This result further supports hypothesis that creating a defect along the Medio-Lateral plane will not significantly alter the strength of the nail, provided they are in the zone of neutral axis of the nail.

The invention claimed is:

1. An interlocking nail (10) for the fixation of transverse and short spiral fractures of long bone particularly shaft of the femur, tibia and humerus having holes for fixing interlocking bolts, wherein:
   the said interlocking nail (10) comprises:
   a. graft extrusion space/slot (101) for holding stem cells graft
   b. endo-screws (108, 109 and 110);
   c. Distal Graft Blocking Plastic Plug (DGBPP) (111); and
   d. Proximal Graft Compressive Plastic Plug (PGCPP) (112);
   a metallic spring is attached on the upper end of Proximal Graft Compressive Plastic Plug (PGCPP) (112) and another end of said metallic spring is attached to metallic circular bar;
   said Endo Compression Screws (108 and 109) create constant static compression on the autograft;
   said compression results in the activation and division of bone cells into bone forming cells as well as reduction bone gap; and
   maximum compression is achieved at the fracture site, irrespective of weight bearing cycle.

2. The interlocking nail (10) as claimed in claim 1, wherein said interlocking nail (10) is a hollow cylinder having an outer diameter ranging from 8 to 13 mm and length ranging from 260-400 mm.

3. The interlocking nail (10) as claimed in claim 1, wherein said interlocking nail (10) is used for fixation of fractures of transverse and short spiral fractures of long bone shaft of the femur, tibia and humerus.

4. The interlocking nail (10) as claimed in claim 1, wherein said holes (103, 104, 105 and 106) are oriented along the line perpendicular to central axis of nail and on opposing surface, across whole thickness at the corresponding level.

5. The interlocking nail (10) as claimed in claim 1, wherein both proximal part (103 and 104) and distal part (105 and 106) have two holes.

6. The interlocking nail (10) as claimed in claim 1, wherein said graft extrusion space/slot (101) holds stem cells graft, preferably from marrow cell or cancellous bone graft (autograft), which enhances healing and fixation of fracture, manifolds.

7. The interlocking nail (10) as claimed in claims 1 or 6, wherein the marrow cell or cancellous graft is obtained from medullary cavity of bone which is being operated.

8. The interlocking nail (10) as claimed in claim 1 or 6, wherein said graft extrusion space (101) is approximately 10 mm in length from medial to lateral direction i.e. from side to side.

9. The interlocking nail (10) as claimed in claim 6, wherein said slot can be on single or both opposing faces in the Medio-Lateral Plane.

10. The interlocking nail (10) as claimed in claim 1, wherein said graft extrusion space (101) is threaded internally from 10 mm above and 5 mm below the margin of graft extrusion space (101).

11. The interlocking nail (10) as claimed in claim 10, wherein said internal threading (102-D) leads to compression of bone graft between Graft Stop-Endo Compression Screw (108) and Graft Compression Screw (109).

12. The interlocking nail (10) as claimed in claim 11, wherein said compression of the Endo Compression Screws (108 and 109) stimulates plurio-potent stem cell for bone formation and bone healing.

13. The interlocking nail (10) as claimed in claim 1, wherein Endo-Compression Screw (110) is inserted from the proximal end of the nail (10) creating compression with tightening of the Endo Compression Screw (110), resulting in the movement at fracture site along the axis of nail (10).

14. The interlocking nail (10) as claimed in claim 1, wherein after putting the said Distal Graft Blocking Plastic Plug (DGBPP) (111) which is blocked by distal screw, the bone graft and the marrow cells are inserted.

15. The interlocking nail (10) as claimed in claim 1, wherein said Proximal Graft Compressive Plastic Plug (PGCPP) (112) is inserted after insertion of Distal Graft Blocking Plastic Plug (DGBPP) (111).

16. The interlocking nail (10) as claimed in claim 1, wherein compression created by Endo Compression Screw is transferred to Proximal Graft Compressive Plastic Plug (PGCPP) (112) through $2^{nd}$ Proximal Screw (104-S) and pulls distal part of fractured bones towards proximal broken end of bone.

17. The interlocking nail (10) as claimed in claim 1, wherein said compression achieved at the fracture site irrespective of weight bearing cycle, results in enhanced bone healing.

* * * * *